US007302723B2

(12) United States Patent
Dean

(10) Patent No.: US 7,302,723 B2

(45) Date of Patent: Dec. 4, 2007

(54) FIRE RESCUE BELT

(76) Inventor: Michael Joseph Dean, 6424 W. Jones Rd., Muncie, IN (US) 47302

( * ) Notice: Subject to any disclaimer, the term of this patent is extended or adjusted under 35 U.S.C. 154(b) by 563 days.

(21) Appl. No.: 10/872,884

(22) Filed: Jun. 21, 2004

(65) Prior Publication Data

US 2004/0255366 A1 Dec. 23, 2004

Related U.S. Application Data

(60) Provisional application No. 60/480,814, filed on Jun. 23, 2003.

(51) Int. Cl.
*A61F 5/37* (2006.01)

(52) U.S. Cl. .............................. 5/627; 5/626; 128/875; 128/876

(58) Field of Classification Search ............ 5/625–628, 5/89.1; 294/140; 128/870, 875, 876; 224/156, 224/158; 280/19

See application file for complete search history.

(56) References Cited

U.S. PATENT DOCUMENTS

| | | | | |
|---|---|---|---|---|
| 2,788,530 A | | 4/1957 | Ferguson | |
| 3,013,282 A | * | 12/1961 | Volavsek | 5/627 |
| 4,124,908 A | | 11/1978 | Burns | |
| 4,442,557 A | | 4/1984 | Clemens | |
| 4,449,253 A | | 5/1984 | Hettinger | |
| 4,679,260 A | | 7/1987 | Frettem | |
| 4,790,040 A | | 12/1988 | Grilliot | |
| 5,050,254 A | | 9/1991 | Murphy | |
| 5,189,746 A | | 3/1993 | Horie | |
| 5,386,604 A | | 2/1995 | Ricketts | |
| 5,720,303 A | | 2/1998 | Richardson | |
| 5,787,529 A | * | 8/1998 | Landes | 5/628 |
| 5,839,137 A | * | 11/1998 | Butler et al. | 5/627 |
| 6,634,044 B1 | * | 10/2003 | Wright | 5/625 |
| 6,851,145 B2 | * | 2/2005 | Smith et al. | 5/627 |
| 6,871,368 B2 | * | 3/2005 | Calkin | 5/628 |

* cited by examiner

*Primary Examiner*—Michael Trettel

(74) *Attorney, Agent, or Firm*—John D Ritchison; Ritchison Law Offices, PC

(57) ABSTRACT

An apparatus generally used as a rescue device that a firefighter or other personnel may use to pull or carry a victim out of a fire or away from a place or peril. The device may be utilized by one single person to rescue another person. The new rescue device is made from standard web materials that are sewn in place and has a web belt feature built in to permit the rescuer to secure the victim. The belt of the device encircles the victim and is fastened at the ends of the belt. The device then is used to pull the victim to safety.

20 Claims, 4 Drawing Sheets

FIRE RESCUE BELT

CROSS-REFERENCE TO RELATED APPLICATIONS

This application claims the benefit of Provisional Patent Application Ser. No. 60/480,814 filed Jun. 23, 2003 by Michael Joseph Dean and titled "FIRE RESCUE BELT".

FIELD OF INVENTION

The present invention relates generally to a rescue device that a firefighter or other personnel may use to carry a victim out of a fire or away from a place of peril. The device may be utilized by one single person to rescue another person.

The new rescue device is made from standard materials and has features built in to make is use both functional and simple to operate. The rescue device has various improvements that will be discussed below. Other prior art does not suggest or disclose the features of the present invention.

FEDERALLY SPONSORED RESEARCH

Not Applicable.

SEQUENCE LISTING OR PROGRAM

Not Applicable

BACKGROUND—FIELD OF INVENTION

The fire rescue belt described in this specification is an apparatus that is designed to easily and quickly provide a rescue device to a fireman in aid of a victim.

A. Introduction of the Problems Addressed

Rescue devices to aid in the removal of victims have traditionally been focused on bulky and cumbersome devices. The devices often require two or more people in order to use the device in rescue. There is a critical need for a simple, lightweight and portable apparatus to aid a fireman or other rescue person in transporting a victim to safety. This is especially important in smoke-filled, perilous situation where a fire response team is separated from each other and a single fireman is faced with transporting a victim by him or herself. Little has been accomplished to provide a simple, compact and single person assist to aid in the transport of a victim. Other prior art does not suggest or disclose the features of the Fire rescue Belt.

B. Prior Art

Rescue and patient transport devices have been featured in a number of U.S. patents since the 1950's. Some devices have attempted to improve upon a transport and rescue device for parts of the problem as stated. In use, the prior art devices were often cumbersome, complex and required two or more people to utilize the device. The new Fire Rescue Belt addresses these limitations and provides a solution to the stated problems.

Examples of prior apparatus for rescuing and transporting victims begin with U.S. Pat. No. 2,788,530 issued to Ferguson (1957). This teaches a large, non-compact device used with rigid poles, complex straps and envelopes to secure a victim. It may be folded into a very large roll for transport as compared to a small compact roll in the new fire rescue belt.

The U.S. Pat. No. 4,124,908 issued to Burns (1978) discloses a rescue and transport device that contains the whole body of a victim. It is comparatively much larger than the new fire rescue belt and requires multiple people to transport a victim. It uses an extensive system of Velcro® connector straps. The U.S. Pat. No. 4,442,557 issued to Clemens (1984) discloses a carrier apparatus for use by fire fighters primarily to carry fire hose, and secondarily to serve as a "sheet-like" personnel carrier. The rather large device, compared to the new fire rescue belt, carries additional hose on a fire truck. Securing straps for the hose are provided, but a victim is transported out with the friction and weight of the victim maintaining them on the "sheet" carrier drug by the fireman.

Another rescue device patented is U.S. Pat. No. 4,449,253 issued to Hettinger (1984). It discloses a fireman's coat modified by the addition of several emergency evacuation straps along the sides, the tops of the shoulders, and behind the neck. These straps permit a fireman overcome by smoke or otherwise incapacitated to be effectively and quickly evacuated by use of the straps as handles to drag or carry the fireman to safety. This is not show use with a non-fireman victim.

Other prior art emergency transport solutions propose various stretcher devices including, Frettem, U.S. Pat. No. 4,679,260 (1987) which discloses a flexible stretcher device for flexibly and adjustably transporting a human body. The flexible stretcher device is comprised of a flexible, carrying and support body member, elongated tubular envelope members, and has a pair of rigid support members for placement in the elongated tubular envelope members. The device is complex, large and rigid compared to the new fire rescue belt presented. A hazard material bag and transport device is taught in U.S. Pat. No. 4,790,040 issued to Grilliot (1988). It provides a "sealable bag" that fully encloses a victim, including the head.

Another patent, issued to Murphy, U.S. Pat. No. 5,050,254 (1991) discloses a large evacuation sheet that can be folded to form an envelope. Several binding straps are provided which serve to secure the two lengths of the web in the face to face relationship and handles are provided which facilitate the lifting of the envelope. The device originally was shown to evacuate by a bedridden patient by lifting them from the bed using the lifting handles. Another emergency patient evacuation system is taught by U.S. Pat. No. 5,189,746 issued to Horie (1993) which shows another sheet-like system with a series of handles and straps. It teaches to enclose the full body with a sheet like material and a rigid bottom.

Still another patent, issued Ricketts, U.S. Pat. No. 5,386,604 (1995) discloses a patient rescue bag provided with an upper portion and a lower portion for use in carrying an injured person from a remote location that is not accessible by normal emergency vehicles. By use of a series of sheets with multiple strips of hook and loop fastener material, the patient rescue bag can be adjusted to the size of the injured person being carried. The portable yet bulky device also teaches the material provides insulation to a victim. Finally, a portable stretcher is taught by U.S. Pat. No. 5,720,303 issued to Richardson (1998) which shows a flexible stretcher which has several straps and requires multiple persons to carry the victim. The stretcher system encircles the whole body of the victim.

While many additional patents could be cited regarding other variations of assemblies, none of these prior art solutions address the problems of either the single person rescue device or the compact and light weight design of the present device. The others are or have not been commercially successful because they are too complex and costly. None of the prior art teaches all the features and capabilities of the Fire Rescue Belt.

SUMMARY OF THE INVENTION

This invention is a fire rescue belt. The device has several features built in that will be described below. These features permit the belt to be small and light enough for a rescue person to carry it into any fire or rescue situation. Though small and light, the belt is designed and configured strong enough to permit a victim to be transported to safety by using the rescue belt.

The main components of this invention are comprised of a strong outer strap that connects a sheet or mesh system of longitudinal and lateral straps to form a "mesh" or "webbing" system. The outer strap at the loop portion may be used as a handle. The outer strap also has a hook or clasp and a ring attached at each end. This permits the belt to be securely fastened after it encircles the victim. The preferred embodiment is shown is the accompanying drawings and pictures.

The materials comprising the device are standard and available from many sources. The materials are primarily the same as utilized in standard rescue and safety equipment. The webbing is strong nylon belting, strong cotton, or the like. The end clasp means can be one of several systems. The one shown in this embodiment is a "quick connecting" snap hook and V-ring. One skilled in the art can appreciate that many variation of the clasp system may be used to permit the scope and spirit of this invention as described below and as depicted in the accompanying drawings.

OBJECTS AND ADVANTAGES

Accordingly, there are several objects and advantages of the Fire Rescue Belt. One advantage of this device over others in the field is that it is small and lightweight. This permits a rescue person to roll it up and carry it in his bunker coat or trouser pockets into the dangerous situation.

Another advantage is its simple and inexpensive design. Because it uses the same materials as other safety equipment, a manufacturer may leverage his material-buying power with a higher volume. Also, the processes to sew or fasten(metal or plastic) the web belt and to attach the clasping system are well known in the industry.

A further advantage is its ease of use. The device is simply unrolled, the victim is placed on the web, and the clasp system is fastened together. This simple manner takes little or no training to use.

An important advantage for the victim is that the loop handle encircles the said victims head and shoulder areas to give that area additional immobility during transport. Another advantage is the device permits a rescuer to use it in low visibility conditions. The victim may be transported out while staying low to the floor or ground and out of the smoke zone.

Finally, other advantages and additional features of the present invention will be more apparent from the accompanying drawings and from the full description of the invention. For one skilled in the art of rescue devices, such as described here, it is readily understood that the features shown in the examples with this invention are readily adapted to other types of rescue devices in the industry.

DESCRIPTION OF THE DRAWINGS—FIGURES

The accompanying drawings, which are incorporated in and constitute a part of this specification, illustrate an embodiment of the present invention that is preferred. The drawings together with the summary description given above and a detailed description given below serve to explain the principles of the invention. It is understood, however, that the invention is not limited to the precise arrangements and instrumentalities shown.

DESCRIPTION OF THE DRAWINGS—REFERENCE NUMERALS

Figure 1:
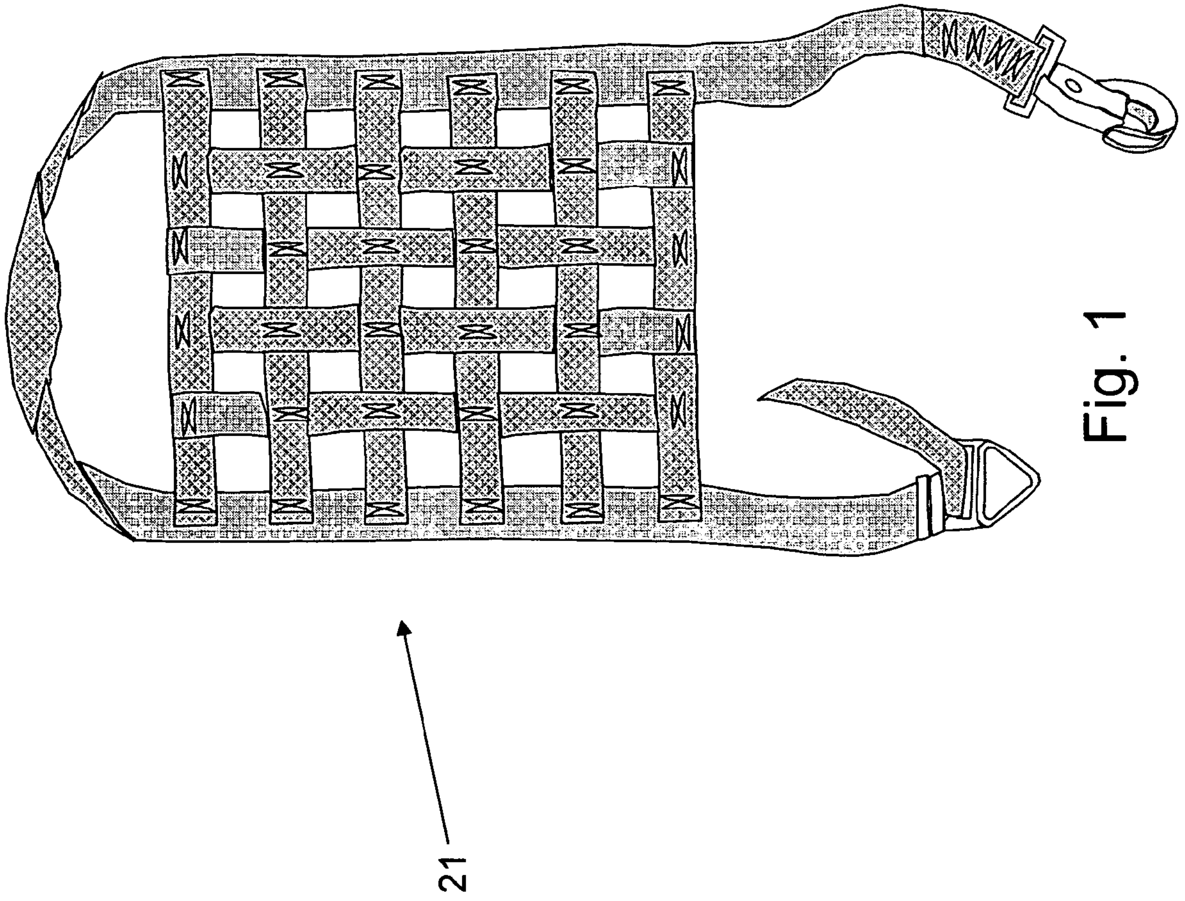
FIG. 1 is a PERSPECTIVE View of the Present Invention.

The following list refers to the drawings:

21 rescue belt
22 outer belt
23 top loop (handle)
24 lateral straps
25 ring
26 hook snap
27 doubled loop
28 clip
29 sewing
30 heavy sewing
31 helmet
32 pocket
33 rolled rescue belt
34 longitudinal straps
35 victim
36 rescuer
37 clasp system
38 arm loops (optional)
39 leg loops (optional)

DETAILED DESCRIPTION OF PERFERRED EMBODIMENT

The present invention is a fire rescue belt. The main components of this invention are comprised of a strong outer strap that connects a series of longitudinal and lateral straps to form a "mesh" or "webbing" system. The outer strap at the loop portion may be used as a handle. The outer strap also has a hook or clasp and a ring attached at each end. This permits the belt to be securely fastened after it encircles the victim.

The materials comprising the device are standard and available from many sources. The webbing is strong nylon or strong cotton belting or the like. The end clasp shown in the embodiment is a "quick connecting" snap hook and ring (V-ring). One skilled in the art can appreciate that many variation of the clasp system may be used to permit the scope and spirit of this invention as described below and as depicted in the accompanying drawings.

The entire device is sewn together with high strength thread or connected by a fastener that is resistant to tearing and to high temperatures. A person having ordinary skill in the field of this invention appreciates the various materials and component parts that may be used to physically permit this rescue belt to be produced and utilized. The improvements over the existing art are providing a device that:

is small and lightweight;

is a simple and inexpensive design;

is easy to use;

supports the head and shoulder area of the victim; and permits a rescuer to use it in low visibility conditions.

In the drawings and illustrations, note well that the FIGS. 1-6 demonstrate the general condition of fire rescue belt. The manner of the device described is functionally understood by those skilled in the art to be appropriate for use in rescuing of victims. One skilled in the art readily appreciates that various other safety devices from similar configurations of the present invention. Therefore, the descriptions are exemplary and not limiting in their nature.

FIG. 1 is a PERSPECTIVE View of the Present Invention with the general embodiment 21 of the present invention is indicated.

Figures 2A, 2B:
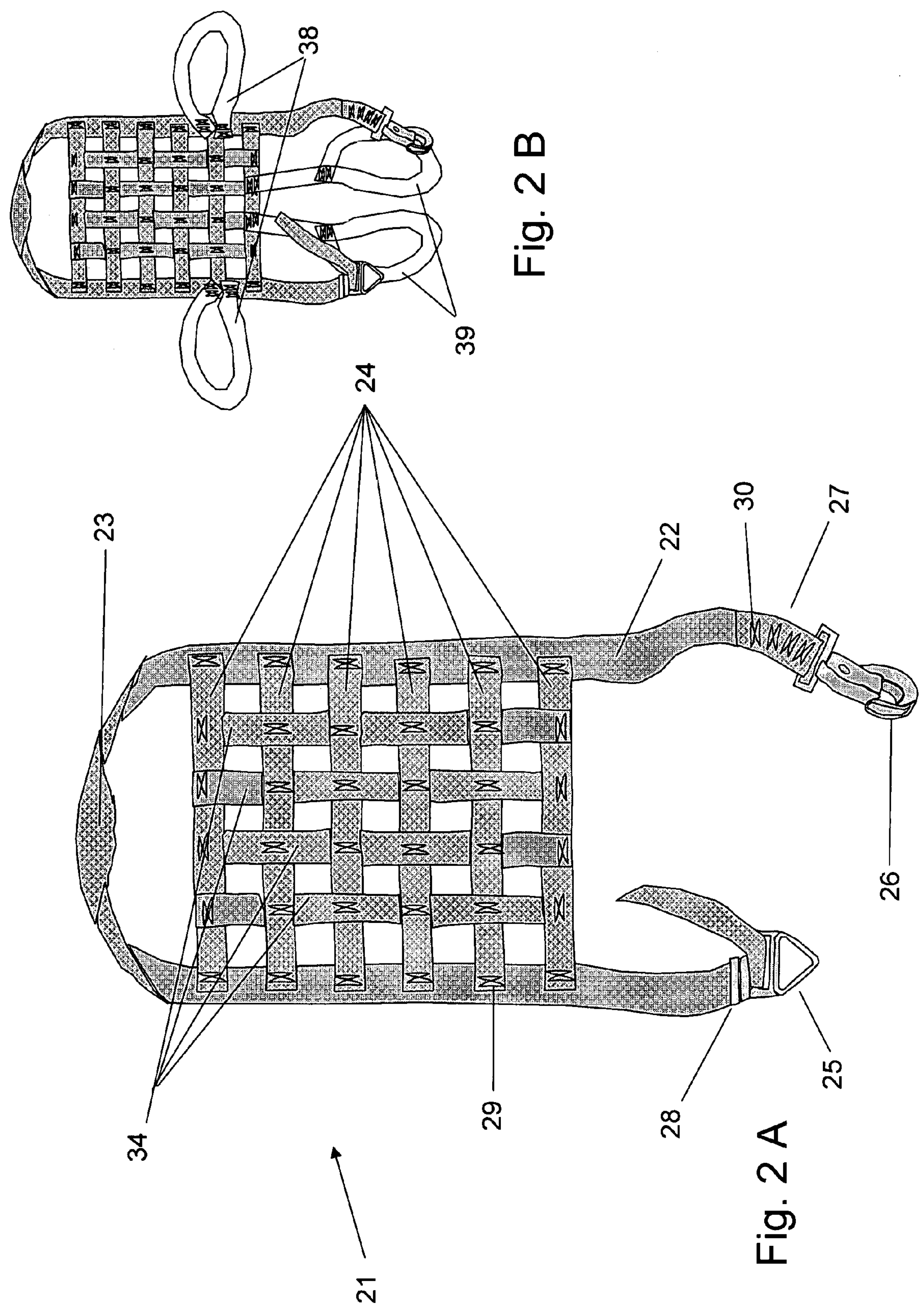
FIG. 2A is a PERSPECTIVE View of the PRESENT INVENTION with many of the component parts indicated.
FIG. 2B is an Alternative embodiment of the PRESENT INVENTION with optional leg and arm loops shown.

FIG. 2A is a PERSPECTIVE View of the PRESENT INVENTION with many of the component parts indicated. The general configuration 21 is indicated. The outer strap 22 encircles the entire device. There are more or less six (6) lateral straps 24 that are sewn 29 to the outer belt 22. There are more or less four (4) longitudinal straps 34 that are sewn to said lateral straps 24. One skilled in the art appreciates that the exact number of the straps can vary with the size of webbing utilized. The six and four are exemplary and not limiting. Additionally, the material that the outer belt 22 and the straps 24 and 34 may be one of a plethora of strong, temperature resistant materials. The prototype shown is mad from a nylon mesh such as used in safety nets on race cars. The configuration and design may be used with various materials as one skilled in the art appreciates.

At one end of the outer belt 22 is a double loop 27. The double loop 27 is heavily sewn 30 into place. The loop 27 here attaches the snap hook 26 into place at one end of the outer belt 22. On the other end of the outer belt 22 is the ring or V-ring 25. It is held in place by the belt clip 28 and permits the outer belt to be adjustable in total length.

Finally, this general FIG. 1 show the top loop 23 which serves as the "handle" of the device. The handle may have additional webbing sewn to it for providing added strength to the area or providing additional padding for comfort.

Figure 3:
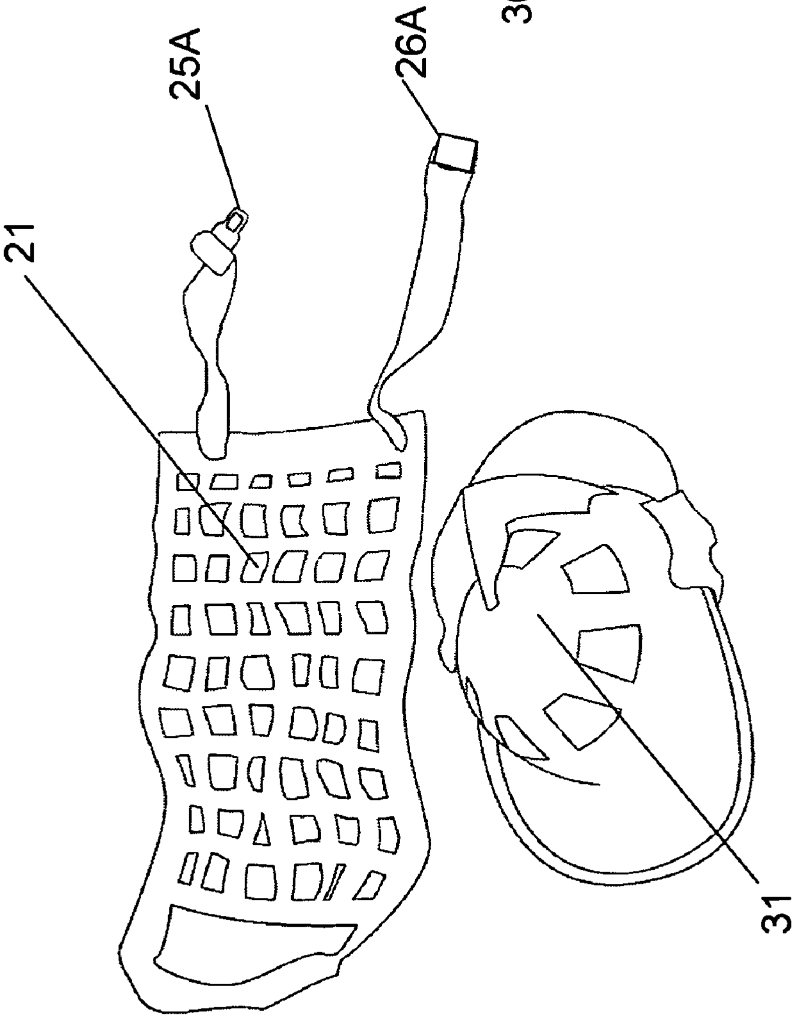
FIG. 3 shows a DRAWING of the device beside a fireman's helmet.

FIG. 3 shows a DRAWING of the device beside a fireman's helmet. The size of the device 21 may be compared to a standard helmet 31.

Figure 4:
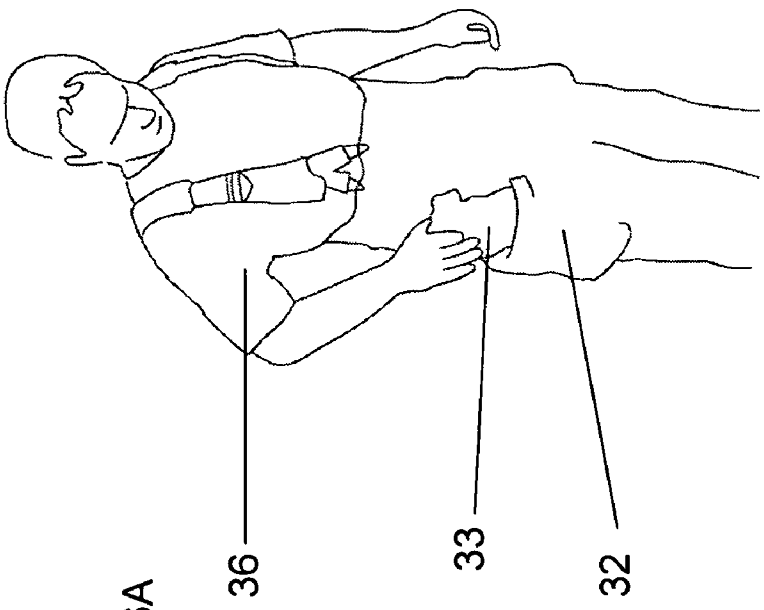
FIG. 4 shows a DRAWING of the device rolled-up and being placed into the fireman's pants pocket.

FIG. 4 shows a DRAWING of the device rolled-up 32 and being placed into the fireman's pants pocket 33. The compact size permits the device to be carried directly with the fireman 36 in his/her pocket or bunker coat (coat not shown).

Figure 5:
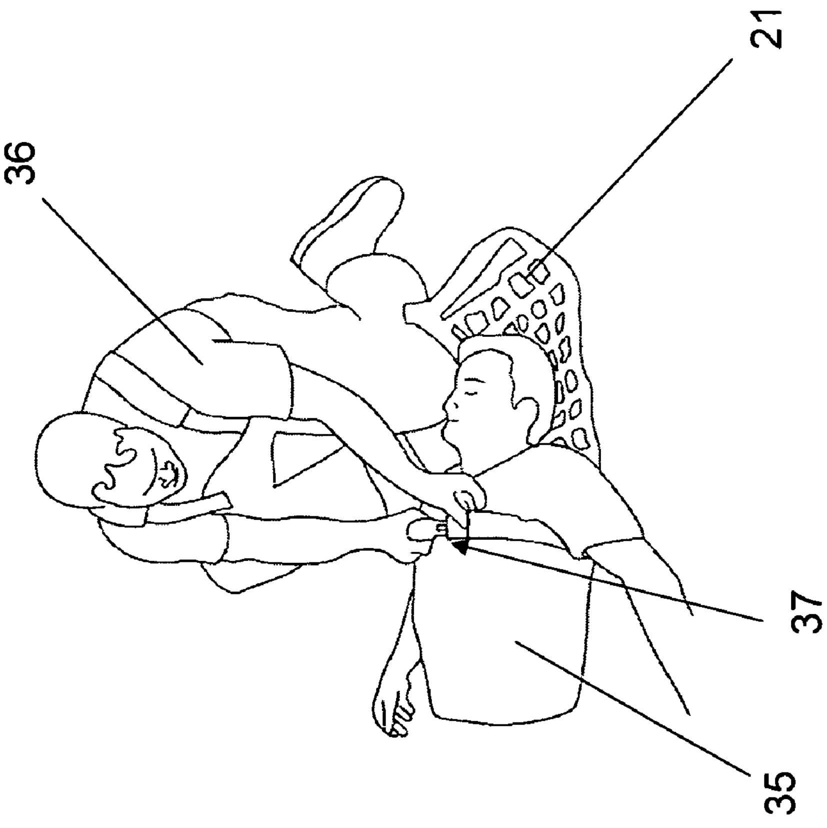
FIG. 5 shows a DRAWING of a victim being placed into the device.

FIG. 5 shows a DRAWING of a victim 35 being placed into the device 21. The rescue person 36 fastens the device at the end of the outer belt 22 and the clasp system 14 is engaged.

Figure 6:
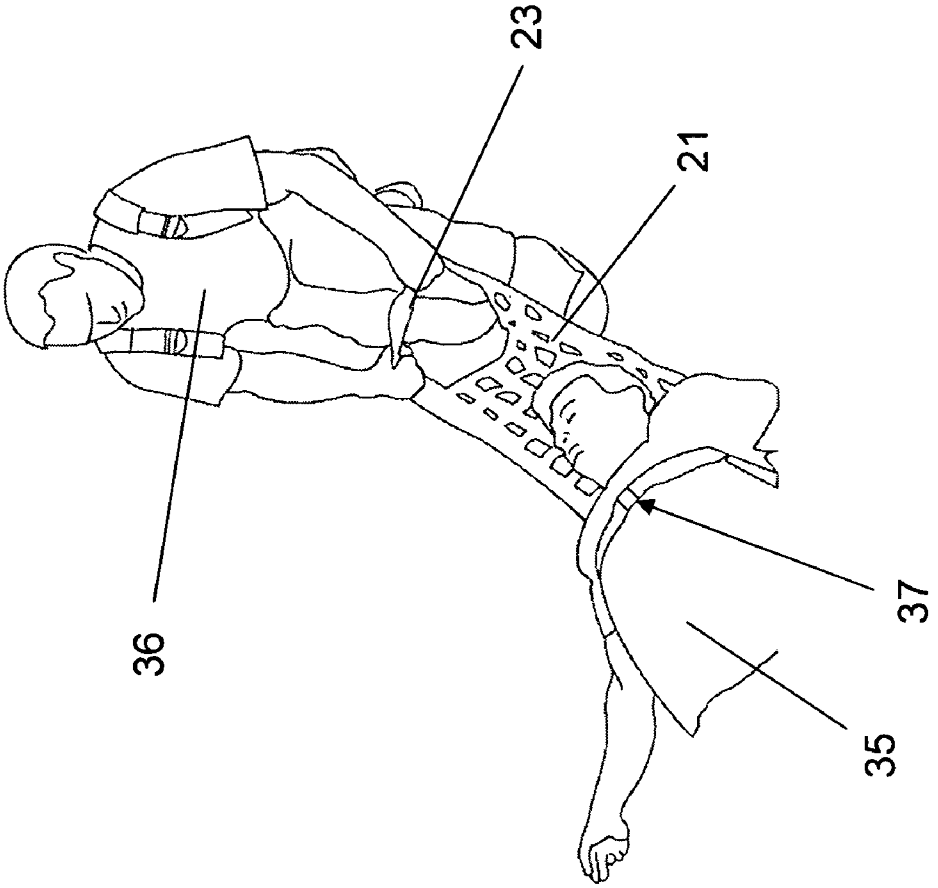
FIG. 6 shows a DRAWING of the rescue belt attached around the victim and the fireman pulling the victim to safety.

FIG. 6 shows a DRAWING of the rescue belt 21 attached around the victim 35. The fireman 36 is pulling the victim 35 to safety by means of the loop handle 23 of the device 21.

In total, all the points and details mentioned here throughout this detailed description of the drawings are exemplary and not limiting. Other components specific to describing a fire rescue belt may be added as a person having ordinary skill in the field of this invention well appreciates. The drawing and components have been focused on the parts shown in respect to the present invention.

OPERATION OF THE PREFERRED EMBODIMENT

The fire rescue belt 21 as the present invention has been described in the above embodiment. The manner of how the invention operates is described below. Note well that the description above and the operation described here must be taken together to fully illustrate the concept of the present invention.

The embodiment described above is a fire rescue belt 21. It is carried in a rolled-up 33 position in a fireman's pocket 32. The fireman 36 may also carry it in his bunker coat (not shown). See FIG. 4. Once the device is needed, the fireman 36 unrolls the device 21 and places the victim 35 on top of the device 21. This is illustrated in FIG. 5. The fireman 36 then engages the clasp system 37 and tightens it around the victim 35. The victim 35 is then pulled to safety by the fireman 36 by using the loop handle 23. See FIG. 6. Once in a safe place, the belt is disengaged, re-rolled into a compact size and placed back in the fireman's pocket 32.

An alternative embodiment for part of the present invention is shown in FIG. 3, above. This view shows a different clasp system of the belt. It is a simple snap in place "automotive type seat belt" 25A and 26A. Other embodiments are easily adapted to this preferred embodiment in addition to the clasp system 37. One may appreciate the desire to add webbing loops for the legs, for the arms or both. These additions are demonstrated as an alternative embodiment in FIG. 2B. They may include one (1) to four (4) loops as desired.

The fire rescue belt 21 as the present invention has been described above in connection with what is presently considered to be the most practical and preferred embodiment. An alternative embodiment that may be used with a standard seat belt connector has also been described. With these descriptions it is to be understood that the invention is not to be limited to the disclosed embodiment. On the contrary, the invention is intended to cover various modifications and equivalent arrangements included within the spirit and scope of the description.

What is claimed as new and desired to be protected by Letters Patent is:

1. A rescue belt apparatus, comprising:

(a) a mesh system of made of a flexible material;

(b) an outer strap that encircles circumferentially the mesh system and that has an extended length of material at each end of the outer strap;

(c) a means to interconnect and secure the mesh system to the outer strap; and (d) a means to releasably connect and secure the ends of the circumferential strap to each other whereby a removable encasement is formed suitable for retaining a victim for a rescue person to drag the victim to safety.

2. The apparatus according to claim 1 wherein the Flexible material is nylon.

3. The apparatus according to claim 1 wherein the Flexible material is cotton.

4. The apparatus according to claim 1 wherein the Flexible material is a flexible composite material.

5. The apparatus according to claim 1 wherein one of the extended ends of the outer strap has an adjustment means to shorten the extended length.

6. The apparatus according to claim 1 wherein the means to interconnect and secure the mesh system to the outer strap is by sewing.

7. The apparatus according to claim 1 wherein the means to interconnect and secure the mesh system to the outer strap is by a fastener.

8. The apparatus according to claim 7 wherein the fastener is metal.

9. The apparatus according to claim 7 wherein the fastener is plastic.

10. The apparatus according to claim 1 wherein the means to releasably connect and secure the ends of the circumferential strap to each other is a hook attached at one end of the extended outer belt and a ring attached at the other end.

11. The apparatus according to claim 10 wherein the ring is a "V" ring.

12. The apparatus according to claim 1 wherein the means to releasably connect and secure the ends of the circumferential strap to each other is an automotive seat belt connection system.

13. The apparatus according to claim 1 wherein there is/are additional loop(s) attached to the apparatus to contain one or more legs and arms of a victim.

14. A rescue belt apparatus, comprising:

(a) a plurality of webbed material straps that are arranged to comprise a flexible mesh system;

(b) an outer strap that encircles circumferentially the mesh system and that has an extended length of material at each end;

(c) a means to interconnect and secure the mesh system to the outer strap; and (d) a means to releasably connect and secure the ends of the circumferential strap to each other whereby a removable encasement is formed suitable for retaining a victim for a rescue person to drag the victim to safety.

15. The apparatus according to claim 14 wherein the means to releasably connect and secure the ends of the circumferential strap to each other is a hook attached at one end of the extended outer belt and a ring attached at the other end.

16. The apparatus according to claim 14 wherein the means to releasably connect and secure the ends of the circumferential strap to each other is an automotive seat belt connection system.

17. The apparatus according to claim 14 wherein the webbed strap material is nylon.

18. The apparatus according to claim 14 wherein the webbed strap material is cotton.

19. The apparatus according to claim 14 wherein the means to interconnect and secure the mesh system to the outer strap is by sewing.

20. The apparatus according to claim 14 wherein the means to interconnect and secure the mesh system to the outer strap is by a fastener.

* * * * *